(12) United States Patent
Carter

(10) Patent No.: US 7,574,256 B2
(45) Date of Patent: Aug. 11, 2009

(54) IONTOPHORETIC DEVICE AND METHOD OF DELIVERY OF ACTIVE AGENTS TO BIOLOGICAL INTERFACE

(75) Inventor: Darrick Carter, Seattle, WA (US)

(73) Assignee: TTI ellebeau, Inc., Tokyo (JP)

( * ) Notice: Subject to any disclaimer, the term of this patent is extended or adjusted under 35 U.S.C. 154(b) by 95 days.

(21) Appl. No.: 11/535,717

(22) Filed: Sep. 27, 2006

(65) Prior Publication Data

US 2007/0088243 A1    Apr. 19, 2007

Related U.S. Application Data

(60) Provisional application No. 60/722,790, filed on Sep. 30, 2005.

(51) Int. Cl.
    *A61N 1/30*      (2006.01)
    *A61F 13/00*      (2006.01)

(52) U.S. Cl. .................................. 604/20; 424/449

(58) Field of Classification Search .................. 604/20, 604/890.1, 89; 514/772; 424/449
See application file for complete search history.

(56) References Cited

U.S. PATENT DOCUMENTS

| | | | |
|---|---|---|---|
| 4,140,121 A | 2/1979 | Kühl et al. ............ 128/260 |
| 4,519,938 A | 5/1985 | Papir ..................... 252/500 |
| 4,722,726 A | 2/1988 | Sanderson et al. ......... 604/20 |
| 4,731,049 A | 3/1988 | Parsi ..................... 604/20 |
| 4,744,787 A | 5/1988 | Phipps et al. ............ 604/20 |
| 4,747,819 A | 5/1988 | Phipps et al. ............ 604/20 |
| 4,752,285 A | 6/1988 | Petelenz et al. .......... 604/20 |
| 4,927,408 A | 5/1990 | Haak et al. .............. 604/20 |
| 4,931,046 A | 6/1990 | Newman ................ 604/20 |
| 4,940,456 A | 7/1990 | Sibalis et al. ............ 604/20 |
| 5,057,072 A | 10/1991 | Phipps ................... 604/20 |
| 5,080,646 A | 1/1992 | Theeuwes et al. ......... 604/20 |
| 5,084,006 A | 1/1992 | Lew et al. ............... 604/20 |
| 5,084,008 A | 1/1992 | Phipps ................... 604/20 |
| 5,135,477 A | 8/1992 | Untereker et al. ......... 604/20 |

(Continued)

FOREIGN PATENT DOCUMENTS

EP      0 824 003      2/1998

(Continued)

OTHER PUBLICATIONS

Kwon, I., et al., "Electrically Erodible Polymer Gel for Controlled Release of Drugs," *Nature*, 354(6351):291-3, Nov. 28, 1991.

(Continued)

*Primary Examiner*—Kevin C Sirmons
*Assistant Examiner*—Deanna K Hall
(74) *Attorney, Agent, or Firm*—Seed IP Law Group PLLC

(57) ABSTRACT

An iontophoresis device includes: an active electrode element operable to provide an electrical potential; an inner active agent reservoir comprising: a first compartment having a diluent; a second compartment having an active agent; and a polymer complex layer disposed between the first compartment and the second compartment, the polymer complex being formed by a first hydrophilic polymer and a second hydrophilic polymer via hydrogen bonding. The polymer complex is electrically responsive and disintegrates when an electrical field is applied. The active agent and the diluent become mixed to form a transient solution or dispersion prior to administration of the active agent

24 Claims, 4 Drawing Sheets

U.S. PATENT DOCUMENTS

| | | | |
|---|---|---|---|
| 5,147,296 A | 9/1992 | Theeuwes et al. ............. 604/20 |
| 5,162,043 A | 11/1992 | Lew et al. ..................... 604/20 |
| 5,169,383 A | 12/1992 | Gyory et al. ................... 604/20 |
| 5,203,768 A | 4/1993 | Haak et al. ..................... 604/20 |
| 5,224,927 A | 7/1993 | Tapper .......................... 604/20 |
| 5,240,995 A | 8/1993 | Gyory et al. ................... 525/57 |
| 5,290,585 A | 3/1994 | Elton ............................ 427/2 |
| 5,298,017 A | 3/1994 | Theeuwes et al. ............. 604/20 |
| 5,310,404 A | 5/1994 | Gyory et al. ................... 604/20 |
| 5,320,598 A | 6/1994 | Haak et al. |
| 5,326,341 A | 7/1994 | Lew et al. ..................... 604/20 |
| 5,338,490 A | 8/1994 | Dietz et al. ................... 252/500 |
| 5,362,420 A | 11/1994 | Itoh et al. ..................... 252/500 |
| 5,374,241 A | 12/1994 | Lloyd et al. ................... 604/20 |
| 5,380,272 A | 1/1995 | Gross ............................ 604/20 |
| 5,385,543 A | 1/1995 | Haak et al. |
| 5,395,310 A | 3/1995 | Untereker et al. ............. 604/20 |
| 5,405,317 A | 4/1995 | Myers et al. ................... 604/20 |
| 5,415,866 A | 5/1995 | Zook ............................ 424/448 |
| 5,423,737 A | 6/1995 | Cartmell et al. ............... 602/57 |
| 5,423,739 A | 6/1995 | Phipps et al. .................. 604/20 |
| 5,489,624 A | 2/1996 | Kantner et al. ............... 524/376 |
| 5,496,266 A | 3/1996 | Haak et al. ..................... 604/20 |
| 5,503,632 A | 4/1996 | Haak .............................. 604/20 |
| 5,536,768 A | 7/1996 | Kantner et al. ............... 524/376 |
| 5,540,654 A | 7/1996 | Riviere et al. ................. 604/20 |
| 5,543,098 A | 8/1996 | Myers et al. ................... 264/104 |
| 5,573,503 A | 11/1996 | Untereker et al. ............. 604/20 |
| 5,573,668 A | 11/1996 | Grosh et al. ................... 210/490 |
| 5,582,587 A | 12/1996 | Gyory et al. |
| 5,637,084 A | 6/1997 | Kontturi et al. ............... 604/20 |
| 5,647,844 A | 7/1997 | Haak et al. ..................... 604/20 |
| 5,660,178 A | 8/1997 | Kantner et al. ............... 128/640 |
| 5,668,170 A | 9/1997 | Gyory .......................... 514/449 |
| 5,711,761 A | 1/1998 | Untereker et al. ............. 604/20 |
| 5,718,913 A | 2/1998 | Dhuique-Mayer et al. .. 424/449 |
| 5,738,647 A | 4/1998 | Bernhard et al. .............. 604/20 |
| 5,770,627 A | 6/1998 | Inoue et al. ............... 514/772.1 |
| 5,788,666 A | 8/1998 | Atanasoska ................... 604/20 |
| 5,795,321 A | 8/1998 | McArthur et al. ............. 604/20 |
| 5,800,685 A | 9/1998 | Perrault ........................ 204/291 |
| 5,837,281 A | 11/1998 | Iga et al. ........................ 424/449 |
| 5,840,056 A | 11/1998 | Atanasoska ................... 604/20 |
| 5,871,460 A | 2/1999 | Phipps et al. .................. 604/20 |
| 5,882,677 A | 3/1999 | Kupperblatt ................. 424/449 |
| 5,891,581 A | 4/1999 | Simpson et al. .............. 428/458 |
| 5,894,021 A | 4/1999 | Okabe et al. .................. 424/449 |
| 5,909,905 A | 6/1999 | Simpson et al. ............. 29/25.35 |
| 5,928,185 A | 7/1999 | Muller et al. .................. 604/20 |
| 5,941,843 A | 8/1999 | Atanasoska et al. ........... 604/20 |
| 5,976,101 A | 11/1999 | Sibalis ......................... 604/20 |
| 5,990,179 A | 11/1999 | Gyory et al. ................. 514/970 |
| 5,991,655 A | 11/1999 | Gross et al. .................... 604/20 |
| 5,995,869 A | 11/1999 | Cormier et al. ................ 604/20 |
| 6,006,130 A | 12/1999 | Higo et al. ..................... 604/20 |
| 6,032,073 A | 2/2000 | Effenhauser ................... 604/20 |
| 6,064,908 A | 5/2000 | Muller et al. .................. 604/20 |
| 6,110,488 A | 8/2000 | Hoffmann ................... 424/449 |
| 6,119,036 A | 9/2000 | Allen, Jr. ...................... 604/20 |
| 6,169,920 B1 | 1/2001 | Haak et al. ..................... 604/20 |
| 6,197,324 B1 | 3/2001 | Crittenden .................. 424/423 |
| 6,256,533 B1 | 7/2001 | Yuzhakov et al. ............. 604/21 |
| 6,275,728 B1 | 8/2001 | Venkatraman et al. ........ 604/20 |
| 6,289,241 B1 | 9/2001 | Phipps ........................ 604/20 |
| 6,312,612 B1 | 11/2001 | Sherman et al. ................ 216/2 |
| 6,329,488 B1 | 12/2001 | Terry et al. .................... 528/28 |
| 6,330,471 B1 | 12/2001 | Higo et al. ..................... 604/20 |
| 6,334,856 B1 | 1/2002 | Allen et al. ................... 604/191 |
| 6,350,259 B1 | 2/2002 | Sage, Jr. et al. ............. 604/501 |
| 6,374,136 B1 * | 4/2002 | Murdock ..................... 604/20 |
| 6,375,963 B1 | 4/2002 | Repka et al. ................. 424/402 |
| 6,377,847 B1 | 4/2002 | Keusch et al. ................. 604/20 |
| 6,377,848 B1 | 4/2002 | Garde et al. ................... 604/20 |
| 6,379,324 B1 | 4/2002 | Gartstein et al. .............. 604/22 |
| 6,385,488 B1 | 5/2002 | Flower et al. ................. 604/20 |
| 6,394,994 B1 | 5/2002 | Vilambi et al. .............. 604/501 |
| 6,402,732 B1 | 6/2002 | Flower et al. ............... 604/501 |
| 6,451,240 B1 | 9/2002 | Sherman et al. ............. 264/504 |
| 6,471,903 B2 | 10/2002 | Sherman et al. .......... 264/328.1 |
| 6,496,727 B1 | 12/2002 | Bernhard et al. .............. 604/20 |
| 6,503,231 B1 | 1/2003 | Prausnitz et al. ............. 604/272 |
| 6,511,463 B1 | 1/2003 | Wood et al. ................. 604/272 |
| 6,522,919 B1 | 2/2003 | Flower et al. ................. 604/20 |
| 6,532,386 B2 | 3/2003 | Sun et al. ....................... 604/20 |
| 6,533,949 B1 | 3/2003 | Yeshurun et al. .............. 216/11 |
| 6,553,255 B1 | 4/2003 | Miller et al. ................... 604/20 |
| 6,565,532 B1 | 5/2003 | Yuzhakov et al. ............ 604/142 |
| 6,576,712 B2 | 6/2003 | Feldstein et al. ............ 525/326.9 |
| 6,584,349 B1 | 6/2003 | Sage, Jr. et al. ............... 604/20 |
| 6,596,401 B1 | 7/2003 | Terry et al. .................. 428/447 |
| 6,603,987 B2 | 8/2003 | Whitson ..................... 600/345 |
| 6,611,707 B1 | 8/2003 | Prausnitz et al. .............. 604/21 |
| 6,629,968 B1 | 10/2003 | Jain et al. ..................... 604/501 |
| 6,635,045 B2 | 10/2003 | Keusch et al. ............... 604/501 |
| 6,654,635 B1 | 11/2003 | Koga et al. .................... 604/20 |
| 6,663,820 B2 | 12/2003 | Arias et al. .................. 264/496 |
| 6,678,554 B1 | 1/2004 | Sun et al. ....................... 604/20 |
| 6,678,555 B2 | 1/2004 | Flower et al. ................. 604/20 |
| 6,692,456 B1 | 2/2004 | Eppstein et al. ............... 604/22 |
| 6,731,977 B2 | 5/2004 | Beck ............................ 604/20 |
| 6,767,341 B2 | 7/2004 | Cho ........................... 604/272 |
| 6,775,569 B2 | 8/2004 | Mori et al. ..................... 604/20 |
| 6,790,372 B2 | 9/2004 | Roy et al. ..................... 216/10 |
| 6,797,276 B1 | 9/2004 | Glenn et al. ............... 424/278.1 |
| 6,803,420 B2 | 10/2004 | Cleary et al. ................. 525/205 |
| 6,808,522 B2 * | 10/2004 | Richards et al. ........... 604/890.1 |
| 6,815,360 B1 | 11/2004 | Canham et al. .............. 438/706 |
| 6,858,018 B1 | 2/2005 | Green et al. ................... 604/19 |
| 6,862,473 B2 | 3/2005 | Keusch et al. ................. 604/20 |
| 6,881,203 B2 | 4/2005 | Delmore et al. ............. 604/272 |
| 6,908,453 B2 | 6/2005 | Fleming et al. ............. 604/173 |
| 6,908,681 B2 | 6/2005 | Terry et al. .................. 428/447 |
| 6,918,901 B1 | 7/2005 | Theeuwes et al. ........... 604/500 |
| 6,939,311 B2 | 9/2005 | Geiger ........................ 600/573 |
| 6,975,902 B2 | 12/2005 | Phipps et al. .................. 604/20 |
| 7,018,370 B2 | 3/2006 | Southam et al. ............. 604/501 |
| 7,054,682 B2 | 5/2006 | Young et al. ................... 604/20 |
| 7,392,080 B2 | 6/2008 | Eppstein et al. ............... 604/20 |
| 2002/0035346 A1 | 3/2002 | Reynolds et al. .............. 604/20 |
| 2003/0065305 A1 | 4/2003 | Higuchi et al. .............. 604/501 |
| 2004/0071765 A1 | 4/2004 | Adachi et al. ............... 424/449 |
| 2004/0087671 A1 | 5/2004 | Tamada et al. ................ 516/99 |
| 2004/0105834 A1 | 6/2004 | Singh et al. ................ 424/70.13 |
| 2004/0143210 A1 | 7/2004 | Shevlin ......................... 604/20 |
| 2004/0166147 A1 | 8/2004 | Lundy et al. ................. 424/449 |
| 2004/0167459 A1 | 8/2004 | Higuchi et al. ................ 604/20 |
| 2004/0225253 A1 | 11/2004 | Shevlin ......................... 604/20 |
| 2004/0247655 A1 | 12/2004 | Asmus et al. ................ 424/449 |
| 2005/0070840 A1 | 3/2005 | Matsumura et al. ........... 604/20 |
| 2005/0143686 A1 | 6/2005 | Shevlin ......................... 604/20 |
| 2005/0169976 A1 | 8/2005 | Mori et al. ................... 424/449 |
| 2005/0267440 A1 | 12/2005 | Herman et al. .............. 604/501 |
| 2006/0009730 A2 | 1/2006 | Shevlin ......................... 604/20 |
| 2006/0095001 A1 | 5/2006 | Matsumura et al. ........... 604/20 |
| 2006/0135906 A1 | 6/2006 | Matsumura et al. ........... 604/20 |
| 2006/0235351 A1 | 10/2006 | Matsumura et al. ........... 604/20 |
| 2007/0048362 A1 | 3/2007 | Nakayama et al. .......... 424/449 |
| 2007/0060862 A1 | 3/2007 | Sun et al. ....................... 604/20 |
| 2007/0083185 A1 | 4/2007 | Carter ......................... 604/501 |
| 2007/0083186 A1 | 4/2007 | Carter et al. ................. 604/501 |
| 2007/0088332 A1 | 4/2007 | Akiyama et al. .......... 604/890.1 |
| 2007/0093787 A1 | 4/2007 | Smith ....................... 604/890.1 |
| 2007/0100274 A1 | 5/2007 | Young et al. ................... 604/20 |
| 2007/0110810 A1 | 5/2007 | Smith ......................... 424/486 |

| | | | | | | |
|---|---|---|---|---|---|---|
| 2007/0225632 | A1 | 9/2007 | Rauser et al. .................. 604/20 | JP | 2000-288098 | 10/2000 |
| 2008/0004564 | A1 | 1/2008 | Smith ........................... 604/20 | JP | 2001-070459 | 3/2001 |
| 2008/0027369 | A1 | 1/2008 | Carter et al. .................. 604/20 | JP | 2001-70459 A | 3/2001 |
| 2008/0033338 | A1 | 2/2008 | Smith ........................... 604/20 | JP | 2001-505091 | 4/2001 |
| 2008/0058701 | A1 | 3/2008 | Smith ........................... 604/20 | JP | 2001-505091 A | 4/2001 |

FOREIGN PATENT DOCUMENTS

| | | |
|---|---|---|
| EP | 1 440 707 A1 | 7/2004 |
| EP | 1 566 197 A1 | 8/2005 |
| JP | 63-35266 | 2/1988 |
| JP | 63-35266 A | 2/1988 |
| JP | 02-206474 | 8/1990 |
| JP | 3-40517 | 2/1991 |
| JP | 08-052224 | 2/1996 |
| JP | 08-503875 | 4/1996 |
| JP | 8-503875 A | 4/1996 |
| JP | 08-164212 | 6/1996 |
| JP | 8-164212 A | 6/1996 |
| JP | 08-317996 | 12/1996 |
| JP | 8-317996 A | 12/1996 |
| JP | 9-248344 | 9/1997 |
| JP | 9-248344 A | 9/1997 |
| JP | 11-076428 | 3/1999 |
| JP | 11-503043 | 3/1999 |
| JP | 11-503956 | 4/1999 |
| JP | 11-503956 A | 4/1999 |
| JP | 11-273452 | 10/1999 |
| JP | 3040517 B2 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000237328 A * | 9/2000 |
| JP | 2000-288097 | 10/2000 |
| JP | 2001-120670 | 5/2001 |
| JP | 2002-541934 | 12/2002 |
| JP | 2002-541934 A | 12/2002 |
| JP | 2004-188188 A | 7/2004 |
| JP | 2004-317317 | 10/2004 |
| JP | 2006-149891 | 6/2006 |
| JP | 2006-212194 | 8/2006 |
| JP | 2006-262943 | 10/2006 |
| JP | 2004-357313 | 12/2007 |
| WO | WO 92/07618 | 5/1992 |
| WO | WO 97/48444 A1 | 12/1997 |
| WO | WO 00/47274 | 8/2000 |
| WO | WO 00/74772 | 12/2000 |
| WO | WO 03/037425 | 5/2003 |
| WO | WO 2007/026672 | 3/2007 |
| WO | WO 2008/027218 A2 | 3/2008 |

OTHER PUBLICATIONS

Malone, E., et al., "Freeform Fabrication of Electroactive Polymer Actuators and Electromechanical Devices," in *Proceedings of the 15th Solid Freeform Fabrication Symposium*, Austin TX, Aug. 2004, pp. 697-708.

U.S. Appl. No. 60/627,952 to Matsumura et al., filed Nov. 16, 2004.

Cabovska, B., "Investigations of Separation Mechanisms in Capillary Electrophoresis and High Performance Liquid Chromatography." (2004) Proquest. UMI No. 3120882.

Zhao, H., "Synthesis and Enzymatic Resolution of Amino Acid Esters in 'Green' Solvents—Ionic Liquids." (2004) Proquest. UMI No. 3111289.

* cited by examiner

IONTOPHORETIC DEVICE AND METHOD OF DELIVERY OF ACTIVE AGENTS TO BIOLOGICAL INTERFACE

CROSS-REFERENCE TO RELATED APPLICATION

This application claims the benefit under 35 U.S.C. § 119 (e) of U.S. Provisional Patent Application No. 60/722,790, filed on Sep. 30, 2005.

BACKGROUND OF THE INVENTION

1. Field of the Invention

This disclosure generally relates to the field of iontophoresis, and more particularly to the delivery of active agents such as therapeutic agents or drugs to a biological interface under the influence of electromotive force and/or current.

2. Description of the Related Art

Iontophoresis employs an electromotive force and/or current to transfer an active agent such as an ionic drug or other therapeutic agent to a biological interface, for example skin or mucus membrane.

Iontophoresis devices typically include an active electrode assembly and a counter electrode assembly, each coupled to opposite poles or terminals of a voltage source, for example a chemical battery. Each electrode assembly typically includes a respective electrode element to apply an electromotive force and/or current. Such electrode elements often comprise a sacrificial element or compound, for example silver or silver chloride.

The active agent may be either cation or anion, and the voltage source can be configured to apply the appropriate voltage polarity based on the polarity of the active agent. Iontophoresis may be advantageously used to enhance or control the delivery rate of the active agent. As discussed in U.S. Pat. No. 5,395,310, the active agent may be stored in a reservoir such as a cavity, or stored in a porous structure or as a gel. In further development of iontophoresis devices, an ion selective membrane may be positioned to serve as a polarity selective barrier between the active agent reservoir and the biological interface, as discussed in U.S. Pat. No. 5,395,310. The membrane, typically only permeable with respect to one particular type of ions, i.e., that of a charged active agent, prevents the back flux of the oppositely charged ions from the skin or mucous membrane.

Stability of the active agent stored in an iontophoresis device is an important factor in assessing the commercial acceptance of iontophoresis devices. Some active agents, including drugs, cannot maintain their chemical integrity or efficacy over long period of time in solution phase. An iontophoresis device that addresses this factor is desirable.

BRIEF SUMMARY OF THE INVENTION

In one embodiment, an iontophoresis device is provided for the delivery of active agents to a biological interface such as skin or mucous membranes, which may provide improved stability of the active agent during storage.

In particular, the device comprises: an active electrode element operable to provide an electrical potential; an inner active agent reservoir comprising: a first compartment having a diluent; a second compartment having an active agent; and a polymer complex layer disposed between the first and second compartments, the polymer complex being formed by a first hydrophilic polymer and a second hydrophilic polymer via hydrogen bonding. The polymer complex is electrically responsive and disintegrates when an electrical field is applied. The active agent and the diluent become mixed to form a transient solution or dispersion prior to administration of the active agent. The device is particular suitable for delivery of active agents that are otherwise unstable in solution phase by allowing for the active agent to be mixed with a diluent immediately prior to the administration.

In another embodiment, a method for transdermal administration of an active agent by iontophoresis is described, the method comprising: positioning an active electrode assembly and a counter electrode assembly of an iontophoresis device on a biological interface of a subject, the active electrode assembly further including an active electrode element operable to provide an electrical potential; and an inner active agent reservoir comprising a first compartment having a diluent, a second compartment having an active agent, and a polymer complex layer disposed between the first compartment and the second compartment, the polymer complex being formed by a first hydrophilic polymer and a second hydrophilic polymer via hydrogen bonding; and applying a sufficient amount of current to cause the polymer complex layer to disintegrate such that the diluent and the active agent are mixed, and to administer a therapeutically effective amount of the active agent in the subject for a limited period of time.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE INVENTION

Figure 1:
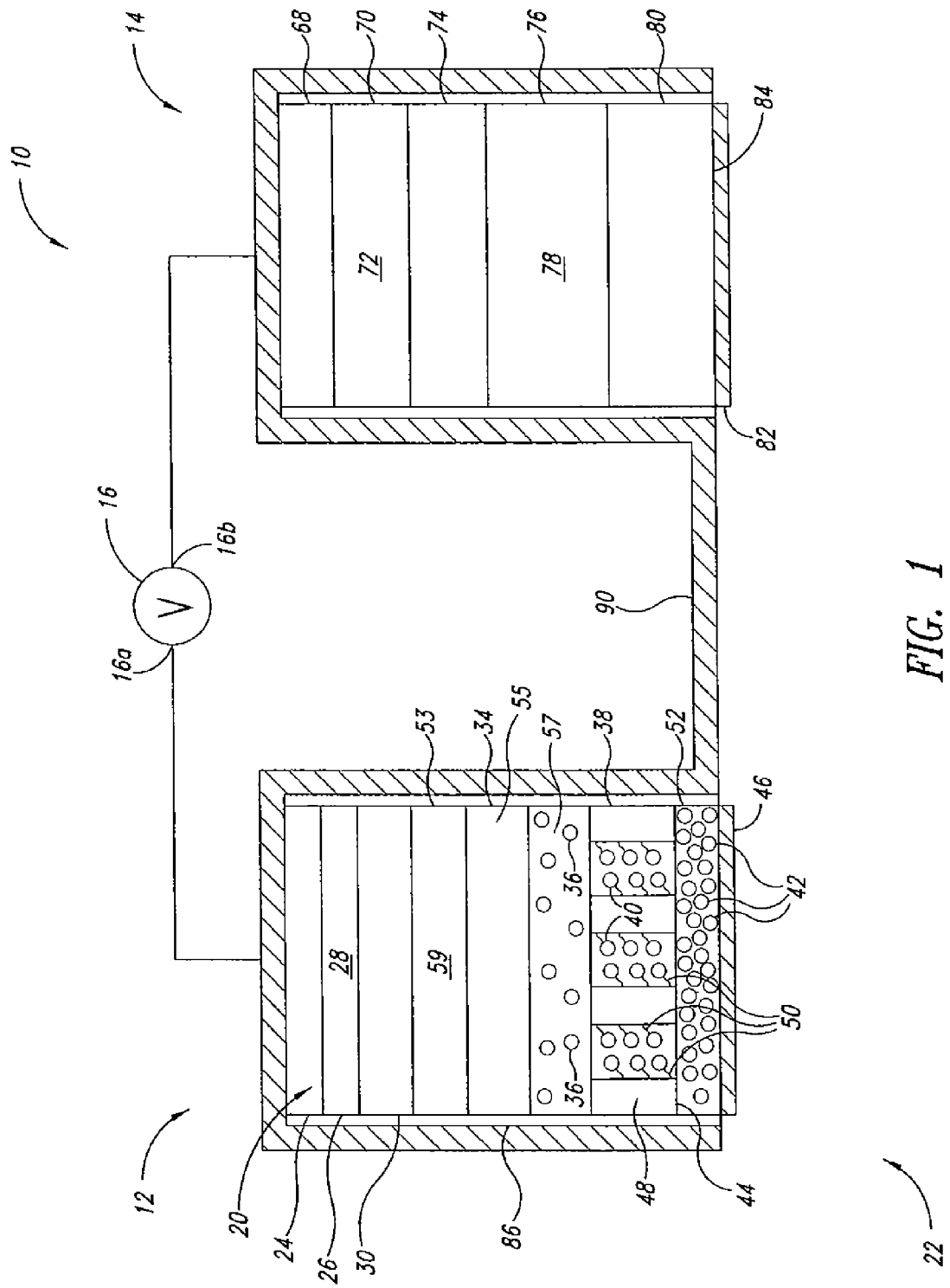
FIG. 1 is a block diagram of an iontophoresis device comprising active and counter electrode assemblies according to one illustrated embodiment, in which the active electrode is a cathode.

The iontophoresis device described herein addresses the stability of an active agent during storage. In particular, the device comprises a compartmentalized inner active agent reservoir including a diluent compartment, an active agent compartment, and a polymer complex layer disposed therebetween. The polymer complex layer acts as a divider between the two compartments. The active agent can be stored in the active agent compartment, either in a stable solution form or in dry form, separate from the diluent. During iontophoresis, the polymer complex layer disintegrates in response to the electrical current, thereby allows the active agent to be mixed with the diluent immediately prior to application to the biological interface. The device is particularly suitable for storing and administering active agents that are typically unstable in a solution phase or although stable in a particular solvent, are incompatible with a pharmaceutically acceptable diluent for extended period of time during storage.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with controllers including but not limited to voltage and/or current regulators have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Generally speaking, during iontophoresis, charged or uncharged species (including active agents), can migrate across a permeable biological interface into the underlying biological tissue. Typically, an iontophoresis device generates both electro-repulsive and electro-osmotic forces. For charged species, the migration is primarily driven by electro-repulsion between the oppositely charged active electrode and the charged species. In addition to the electro-repulsive forces, the electro-osmotic flow of a liquid (e.g., a solvent or diluent) may also contribute to transporting the charged species. In certain embodiments, the electro-osmotic solvent flow is a secondary force that can enhance the migration of the charged species. For uncharged or neutral species, the migration is primarily driven by the electro-osmotic flow of a solvent.

As used herein and in the claims, the term "polymer complex" means a stable complex formed by two hydrophilic polymers due to collective hydrogen bonding between electron-deficient groups of one polymer and electron-rich groups of the other polymer. Under certain conditions, which will be discussed in details below, the complex formation is thermodynamically favorable and confers stability to the complex on account of the large numbers of hydrogen bonding. Unlike each of the polymer component, the complex is not water-soluble.

In one embodiment, a first polymer component for forming the polymer complex comprises an electron-deficient group in each repeating unit. A second polymer component for forming the polymer complex comprises an electron-rich group in each repeating unit. Examples of polymer complexes stabilized by hydrogen bonding included, but are not limited to: poly((meth)acrylic acid) and poly(acrylamide), poly((meth)acrylic acid) and poly(vinyl alcohol), poly ((meth)acrylic acid) and poly(ethylene glycol), poly((meth) acrylic acid) and poly(N-vinylpyrrolidone) and poly((meth) acrylic acid) and poly(ethyloxazoline). Poly((meth)acrylic acid) is an art-recognized expression and refers to both poly (acrylic acid) and poly(methacrylic acid).

In one embodiment, each polymer component has a molecular weight of at least 5,000. In another embodiment, each polymer component has a molecular weight of at least 10,000. In another embodiment, each polymer component has a molecular weight of at least 50,000.

The polymer complex is typically formed at 1:1 ratio of respective repeating units from the first and second polymer components. The complex is generally formed in aqueous media within a narrow range of solvent composition, pH and ion strength. Typically, the complex is stabilized by the cooperative nature of the hydrogen bonding as well as hydrophobic interactions, i.e., the hydrophobic polymer backbones tend to aggregate due to their collective repulsion from water.

As noted above, the complex formation can be triggered by the pH value of the aqueous media. Typically, the electron-rich groups of the second polymer component are sensitive to pH fluctuation and can be protonated at low pH and deprotonated at higher pH. The protonated forms are prone to forming hydrogen bonding with the electron-deficient groups of the first polymer component to provide a stabilized polymer complex.

The complex formation process is reversible. At higher pH, the electron-rich groups are deprotonated. This process weakens or eliminates the hydrogen bonding. In the absence of the hydrogen bonding, the two polymer components become dissociate from each other and the complex disintegrates. As used herein, "critical pH" refers to the pH value or range where the polymer complex becomes unstable.

For instance, poly(acrylic acid) and poly(ethyloxazoline) having 1:1 ratio of repeating units form a water-insoluble complex at pH 5. The complex remains stable for a month at the same pH. The complex dissolves instantly above pH 5.4. This process and its mechanism are described in details in Electrically Erodible Polymer Gel For Controlled Release of Drugs, Kown, I.C., et al., Nature, Vol. 354, 291, 1991, which reference is incorporated herein in its entirety.

Significantly, the disintegration of the polymer complex can be triggered and controlled by an electric field. Under an electric field, hydroxide ions ($OH^-$) may be generated by electrolysis of water, during which water is reduced to hydrogen gas and hydroxide. Hydroxide ions may also be present in an electrolyte. In any event, electrically induced migration of hydroxide ion changes the local pH environment of the polymer complex and leads to its disintegration.

The polymer complex layer of the present device may take either a solid form (e.g., a solid disc) or a pre-swollen gel form. It serves as a divider to separate an active agent compartment from a diluent compartment. During iontophoresis, hydroxide ions, either generated electrochemically or present in an electrolyte solution will migrate to the polymer complex layer and cause its disintegration. Once the polymer complex divider is eliminated, the active agent and the diluent diffuse to form a transient solution or dispersion within the inner active agent reservoir prior to being transported across the biological interface.

"Diluent" as used herein and in the claims refers to any solvent or solvent system that is compatible with the active agent to be delivered. The diluent itself is inactive but is necessary to prepare the active agent prior to its transport across the biological interface. For instance, in one embodiment, the active agent may be stored in a stable solid form and only becomes miscible with a diluent immediately prior to administration. In another embodiment, a stable precursor of an active agent may be suspended in a stable dispersion suitable for long-term storage. The precursor is capable of releasing the free active agent upon being mixed with a diluent. This is particular useful when an active agent is unstable or short-lived, and must be generated immediately prior to administration.

In certain embodiments, an active agent can be solubilized and more importantly ionized in the diluent to attain a net charge. A charged active agent can be primarily driven by electro-repulsion during iontophoresis. In other embodiment, a neutral active agent remains neutral even in the presence of the diluent. Neutral active agents can be transported via electro-osmotic flow of the diluent, as described in more details herein.

Typically, a diluent is aqueous. It may further comprise physiologically compatible ions, such as sodium, potassium, chloride, and phosphate. A diluent may also comprise water-soluble organic solvents such as ethanol and acetone.

"Active agent" refers to a compound, molecule, or treatment that elicits a biological response from any host, animal, vertebrate, or invertebrate, including for example fish, mammals, amphibians, reptiles, birds, and humans. Examples of active agents include therapeutic agents, pharmaceutical agents, pharmaceuticals (e.g., a drug, a therapeutic compound, pharmaceutical salts, and the like) non-pharmaceuticals (e.g., cosmetic substance, and the like), a vaccine, an immunological agent, a local or general anesthetic or painkiller, an antigen or a protein or peptide such as insulin, a chemotherapy agent, an anti-tumor agent.

In some embodiments, the term "active agent" further refers to the active agent, as well as its pharmacologically active salts, pharmaceutically acceptable salts, prodrugs, metabolites, analogs, and the like. In some further embodiment, the active agent includes at least one ionic, cationic, anionic, ionizable, and/or neutral therapeutic drug and/or pharmaceutical acceptable salts thereof.

In some embodiments, the active agent may include one or more "cationic active agents" that are positively charged, and/or are capable of forming positive charges in aqueous media. For example, many biologically active agents have functional groups that are readily convertible to a positive ion or can dissociate into a positively charged ion and a counter ion in an aqueous medium. Other active agents may be polarized or polarizable, that is exhibiting a polarity at one portion relative to another portion. For instance, an active agent having an amine group can typically take the form a quaternary ammonium cation (-NR$_3$H$^+$) at an appropriate pH, also referred to as a protonated amine. As will be discussed in detail below, many active agents, including most of the "caine" class analgesics and anesthetics, comprise amine groups. These amine groups can be present in the iontophoresis device in protonated forms.

In other embodiments, the active agents may include functional groups that can readily converted to contain negatively charges or can dissociate into a negatively charged ion and a counter ion in an aqueous medium. The negatively charged active agents are also referred to as "anionic active agents". For instance, an active agent having a carboxylic acid group can typically take the form of —COOH in solid state and dissociates into a —COO$^-$ in an aqueous medium of appropriate pH. In other embodiments, the active agent may comprise charged functional groups such as —SO$_3^-$, —PO$_4^{2-}$, and the like.

Other active agents may be polarized or polarizable, that is, exhibiting a polarity at one portion relative to another portion.

The term "active agent" may also refer to electrically neutral agents, molecules, or compounds capable of being delivered via electro-osmotic flow. The electrically neutral agents are typically carried by the flow of, for example, a diluent during electrophoresis. Selection of the suitable active agents is therefore within the knowledge of one skilled in the relevant art.

In some embodiments, one or more active agents may be selected from analgesics, anesthetics, anesthetics vaccines, antibiotics, adjuvants, immunological adjuvants, immunogens, tolerogens, allergens, toll-like receptor agonists, toll-like receptor antagonists, immuno-adjuvants, immuno-modulators, immuno-response agents, immuno-stimulators, specific immuno-stimulators, non-specific immuno-stimulators, and immuno-suppressants, or combinations thereof.

Non-limiting examples of such active agents include Lidocaine®, articaine, and others of the -caine class; morphine, hydromorphone, fentanyl, oxycodone, hydrocodone, buprenorphine, methadone, and similar opioid agonists; sumatriptan succinate, zolmitriptan, naratriptan HCl, rizatriptan benzoate, almotriptan malate, frovatriptan succinate and other 5-hydroxytryptaminel receptor subtype agonists; resiquimod, imiquidmod, and similar TLR 7 and 8 agonists and antagonists; domperidone, granisetron hydrochloride, ondansetron and such anti-emetic drugs; zolpidem tartrate and similar sleep inducing agents; L-dopa and other anti-Parkinson's medications: aripiprazole, olanzapine, quetiapine, risperidone, clozapine, and ziprasidone, as well as other neuroleptica; diabetes drugs such as exenatide; as well as peptides and proteins for treatment of obesity and other maladies.

Further non-limiting examples of anesthetic active agents or pain killers include ambucaine, amethocaine, isobutyl p-aminobenzoate, amolanone, amoxecaine, amylocaine, aptocaine, azacaine, bencaine, benoxinate, benzocaine, N,N-dimethylalanylbenzocaine, N,N-dimethylglycylbenzocaine, glycylbenzocaine, beta-adrenoceptor antagonists betoxycaine, bumecaine, bupivicaine, levobupivicaine, butacaine, butamben, butanilicaine, butethamine, butoxycaine, metabutoxycaine, carbizocaine, carticaine, centbucridine, cepacaine, cetacaine, chloroprocaine, cocaethylene, cocaine, pseudococaine, cyclomethycaine, dibucaine, dimethisoquin, dimethocaine, diperodon, dyclonine, ecognine, ecogonidine, ethyl aminobenzoate, etidocaine, euprocin, fenalcomine, fomocaine, heptacaine, hexacaine, hexocaine, hexylcaine, ketocaine, leucinocaine, levoxadrol, lignocaine, lotucaine, marcaine, mepivacaine, metacaine, methyl chloride, myrtecaine, naepaine, octacaine, orthocaine, oxethazaine, parenthoxycaine, pentacaine, phenacine, phenol, piperocaine, piridocaine, polidocanol, polycaine, prilocaine, pramoxine, procaine (Novocaine®), hydroxyprocaine, propanocaine, proparacaine, propipocaine, propoxycaine, pyrrocaine, quatacaine, rhinocaine, risocaine, rodocaine, ropivacaine, salicyl alcohol, tetracaine, hydroxytetracaine, tolycaine, trapencaine, tricaine, trimecaine tropacocaine, zolamine, a pharmaceutically acceptable salt thereof, and mixtures thereof.

As noted above, the device described herein is particularly suitable for delivery of active agents that are otherwise unstable if they remain in a solution phase for any extended period of time. According to one embodiment, such active agents can be stored in solid form and separated from the diluent by a polymer complex layer or divider. In response to an electrical field, the polymer complex divider disintegrates and allows for the active agent to mix with the diluent to provide the active agent transportable under the electromotive force and/or current.

As used herein and in the claims, the term "membrane" means a layer, barrier or material, which may, or may not be permeable. Unless specified otherwise, membranes may take the form a solid, liquid or gel, and may or may not have a distinct lattice or cross-linked structure.

As used herein and in the claims, the term "ion selective membrane" means a membrane that is substantially selective to ions, passing certain ions while blocking passage of other ions. An ion selective membrane for example, may take the form of a charge selective membrane, or may take the form of a semi-permeable membrane.

As used herein and in the claims, the term "ion selective membrane" or "charge selective membrane" means a membrane, which substantially passes and/or substantially blocks ions based primarily on the polarity or charge carried by the ion. Charge selective membranes are typically referred to as ion exchange membranes, and these terms are used interchangeably herein and in the claims. Charge selective or ion exchange membranes may take the form of a cation exchange membrane, an anion exchange membrane, and/or a bipolar membrane.

A cation exchange membrane permits only the passage of cations and substantially blocks anions. Examples of commercially available cation exchange membranes include those available under the designators NEOSEPTA, CM-1, CM-2, CMX, CMS, and CMB from Tokuyama Co., Ltd. Conversely, an anion exchange membrane permits only the passage of anions and substantially blocks cations. Examples of commercially available anion exchange membranes include those available under the designators NEOSEPTA, AM-1, AM-3, AMX, AHA, ACH and ACS also from Tokuyama Co., Ltd.

As used herein and in the claims, term "bipolar membrane" means a membrane that is selective to two different charges or polarities. Unless specified otherwise, a bipolar membrane may take the form of a unitary membrane structure or multiple membrane structure. The unitary membrane structure may have a first portion including cation ion exchange material or groups and a second portion opposed to the first portion, including anion ion exchange material or groups. The multiple membrane structure (e.g., two film) may be formed by a cation exchange membrane attached or coupled to an anion exchange membrane. The cation and anion exchange membranes initially start as distinct structures, and may or may not retain their distinctiveness in the structure of the resulting bipolar membrane.

As used herein and in the claims, the term "semi-permeable membrane" means a membrane that substantially selective based on a size or molecular weight of the ion. Thus, a semi-permeable membrane substantially passes ions of a first molecular weight or size, while substantially blocking passage of ions of a second molecular weight or size, greater than the first molecular weight or size.

As used herein and in the claims, the term "porous membrane" means a membrane that is not substantially selective with respect to ions at issue. For example, a porous membrane is one that is not substantially selective based on polarity, and not substantially selective based on the molecular weight or size of a subject element or compound.

As used herein and in the claims, the term "reservoir" means any form of mechanism to retain an element or compound in a liquid state, solid state, gaseous state, mixed state and/or transitional state. For example, unless specified otherwise, a reservoir may include one or more cavities formed by a structure, and may include one or more ion exchange membranes, semi-permeable membranes, porous membranes and/or gels if such are capable of at least temporarily retaining an element or compound. Typically, a reservoir serves to retain a plurality of active agent prior to the discharge of such agent by electromotive force and/or current into the biological interface. As discussed above, the device described herein comprises an inner active agent reservoir, which is compartmentalized. A reservoir may also retain an electrolyte solution.

The headings provided herein are for convenience only and do not interpret the scope or meaning of the embodiments.

FIGS. 1-4 show an iontophoresis device 10 comprising active and counter electrode assemblies, 12, 14, respectively. They are electrically coupled to a power source 16, operable to supply an active agent contained in the active electrode assembly 12 to a biological interface 18 (FIG. 3 and 4), such as a portion of skin or mucous membrane via iontophoresis, according to one illustrated embodiment.

In the embodiment illustrated in FIG. 1, the active electrode assembly 12 comprises, from an interior 20 to an exterior 22 of the active electrode assembly 12: an active electrode element 24, an optional electrolyte reservoir 26 storing an electrolyte 28, an optional inner ion selective membrane 30, an inner active agent reservoir 34 having a first compartment 53 having a diluent 59, a second compartment 57 house an active agent 36 and a polymer complex layer 55 disposed between the first and second compartments, an optional outermost ion selective membrane 38 that optionally caches additional active agent 40, an optional further active agent 42 carried by an outer surface 44 of the outermost ion selective membrane 38, and an outer release liner 46. Each of the above elements or structures will be discussed in detail below.

The active electrode element 24 is coupled to a first pole 16a of the power source 16 and positioned in the active electrode assembly 12 to apply an electromotive force or current to transport active agent 36, 40, 42 via various other components of the active electrode assembly 12. In FIG. 1, the active electrode element is a cathode and the active agents 36, 40 and 42 are negatively charged.

The active electrode element 24 may take a variety of forms. In one embodiment, the device may advantageously employ a carbon-based active electrode element 24. Such may, for example, comprise multiple layers, for example a polymer matrix comprising carbon and a conductive sheet comprising carbon fiber or carbon fiber paper, such as that described in commonly assigned pending Japanese patent application 2004/317317, filed Oct. 29, 2004. The carbon-based electrodes are inert electrodes in the sense that they do not themselves undergo or participate in electrochemical reactions. Thus, an inert electrode distributes current without being eroded or depleted, and conducts current through electrolysis of water, i.e., generating ions by either reduction or oxidation of water. Additional examples of inert electrodes include stainless steal, gold, platinum or graphite.

The electrolyte reservoir 26 may take a variety of forms including any structure capable of retaining electrolyte 28, and in some embodiments may even be the electrolyte 28 itself, for example, where the electrolyte 28 is in a gel, semi-solid or solid form. For example, the electrolyte reservoir 26 may take the form of a pouch or other receptacle, a membrane with pores, cavities or interstices, particularly where the electrolyte 28 is a liquid.

In one embodiment, the electrolyte 28 comprises ionic or ionizable components in an aqueous medium, which can act to conduct current towards or away from the active electrode element. Suitable electrolytes include, for example, aqueous solutions of salts. Preferably, the electrolyte 28 includes salts of physiological ions, such as, sodium, potassium, chloride, and phosphate.

As noted above, the electrolyte 28 may be in the form of an aqueous solution housed within a reservoir 26, or in the form of dispersion in a hydrogel or hydrophilic polymer capable of retaining substantial amount of water. For instance, a suitable electrolyte may take the form of a solution of 0.5 M disodium fumarate: 0.5 M poly(acrylic acid).

The inner ion selective membrane 30 is generally positioned to separate the electrolyte 28 and the inner active agent reservoir 34, if such a membrane is to be employed. The inner ion selective membrane 30 may take the form of a charge selective membrane. For example, because the active agent 36, 40, 42 comprises an negatively charged active agent, the inner ion selective membrane 30 may take the form of a cation exchange membrane, selective to substantially pass cations and substantially block the anionic active agent. The inner ion selective membrane 30 may advantageously prevent transfer of undesirable elements or compounds between the electrolyte 28 and the inner active agent reservoir 34. For example, the inner ion selective membrane 30 may prevent or inhibit the transfer of chloride (Cl$^-$) ions from the electrolyte 28, thereby increases the transfer rate and/or biological compatibility of the iontophoresis device 10.

The inner active agent reservoir 34 is generally positioned between the inner ion selective membrane 30 and the outermost ion selective membrane 38. The inner active agent reservoir 34 may take a variety of forms including any structure capable of temporarily retaining active agent 36. For example, the inner active agent reservoir 34 may take the form of a pouch or other receptacle, a membrane with pores, cavities or interstices, particularly where the active agent 36 is a liquid. The inner active agent reservoir 34 further comprises a first compartment 53 having a diluent 59, a second compartment 57 having a plurality of active agent 36, and a polymer complex layer 55 disposed between the first compartment 53 and the second compartment 57. The polymer complex layer 55 forms a divider or boundary separating the first and second compartments. Upon disintegration of the layer 55, the respective contents the first and second compartments, i.e., the diluent 59 and the active agent 36, are mixed.

The diluent may be maintained at a pH during storage by a buffer solution at below the critical pH at which point the polymer complex may become unstable. In one embodiment, the diluent includes water. Under the application of an electrical field, the water in the diluent compartment 53 can be electrolyzed and hydroxide ions are generated as an electrochemical product of the reduction of water in the active electrode assembly 12 (a cathode). The hydroxide ions migrate away from the cathode 12 due to electro-repulsion. They further cause an increase in the pH in the local environment of the polymer complex layer 55. The hydrogen bonding of the polymer complex is compromised and the layer 55 disintegrates. As a result, the active agents 36 and the diluent 59 are mixed and the active agents 36 migrate toward the biological interface under the electro-repulsion and/or electro-osmotic forces.

Optionally, an outermost ion selective membrane 38 is positioned generally opposed across the active electrode assembly 12 from the active electrode element 24. The outermost membrane 38 may, as in the embodiment illustrated in FIGS. 1-4, take the form of an ion exchange membrane, pores 48 (only one called out in FIGS. 1 and 2 for sake of clarity of illustration) of the ion selective membrane 38 including ion exchange material or groups 50 (only three called out in FIGS. 1-4 for sake of clarity of illustration). Under the influence of an electromotive force or current, the ion exchange material or groups 50 selectively substantially passes ions of the same polarity as active agent 36, 40, 42, while substantially blocking ions of the opposite polarity. Thus, the outermost ion exchange membrane 38 is charge selective. Where the active agent 36, 40, 42 is an anion, the outermost ion selective membrane 38 may take the form of an anion exchange membrane, thus allowing the passage of the anionic active agent while blocking the back flux of the cations present in the biological interface, such as skin.

The outermost ion selective membrane 38 may optionally cache active agent 40. In particular, the ion exchange groups or material 50 temporarily retains ions of the same polarity as the polarity of the active agent in the absence of electromotive force or current and substantially releases those ions when replaced with substitutive ions of like polarity or charge under the influence of an electromotive force or current.

Alternatively, the outermost ion selective membrane 38 may take the form of semi-permeable or microporous membrane which is selective by size. In some embodiments, such a semi-permeable membrane may advantageously cache active agent 40, for example by employing the removably releasable outer release liner 46 to retain the active agent 40 until the outer release liner 46 is removed prior to use.

The outermost ion selective membrane 38 may be optionally preloaded with the additional active agent 40, such as ionized or ionizable drugs or therapeutic agents and/or polarized or polarizable drugs or therapeutic agents. Where the outermost ion selective membrane 38 is an ion exchange membrane, a substantial amount of active agent 40 may bond to ion exchange groups 50 in the pores, cavities or interstices 48 of the outermost ion selective membrane 38.

The active agent 42 that fails to bond to the ion exchange groups of material 50 may adhere to the outer surface 44 of the outermost ion selective membrane 38 as the further active agent 42. Alternatively, or additionally, the further active agent 42 may be positively deposited on and/or adhered to at least a portion of the outer surface 44 of the outermost ion selective membrane 38, for example, by spraying, flooding, coating, electrostatically, vapor deposition, and/or otherwise. In some embodiments, the further active agent 42 may sufficiently cover the outer surface 44 and/or be of sufficient thickness so as to form a distinct layer 52. In other embodiments, the further active agent 42 may not be sufficient in volume, thickness or coverage as to constitute a layer in a conventional sense of such term.

The active agent 42 may be deposited in a variety of highly concentrated forms such as, for example, solid form, nearly saturated solution form or gel form. If in solid form, a source of hydration may be provided, either integrated into the active electrode assembly 12, or applied from the exterior thereof just prior to use.

In some embodiments, the active agent 36, additional active agent 40, and/or further active agent 42 may be identical or similar compositions or elements. In other embodiments, the active agent 36, additional active agent 40, and/or farther active agent 42 may be different compositions or elements from one another. Thus, a first type of active agent may be stored in the inner active agent reservoir 34, while a second type of active agent may be cached in the outermost ion selective membrane 38. In such an embodiment, either the first type or the second type of active agent may be deposited on the outer surface 44 of the outermost ion selective membrane 38 as the farther active agent 42. Alternatively, a mix of the first and the second types of active agent may be deposited on the outer surface 44 of the outermost ion selective membrane 38 as the further active agent 42. As a further alternative, a third type of active agent composition or element may be deposited on the outer surface 44 of the outermost ion selective membrane 38 as the further active agent 42. In another embodiment, a first type of active agent may be stored in the inner active agent reservoir 34 as the active agent 36 and cached in the outermost ion selective membrane 38 as the additional active agent 40, while a second type of active agent may be deposited on the outer surface 44 of the outermost ion selective membrane 38 as the further active agent 42. Typically, in embodiments where one or more different active agents are employed, the active agents 36, 40, 42 will all be of common polarity to prevent the active agents 36, 40, 42 from competing with one another. Other combinations are possible.

The outer release liner 46 may generally be positioned overlying or covering further active agent 42 carried by the outer surface 44 of the outermost ion selective membrane 38. The outer release liner 46 may protect the further active agent 42 and/or outermost ion selective membrane 38 during storage, prior to application of an electromotive force or current. The outer release liner 46 may be a selectively releasable liner made of waterproof material, such as release liners commonly associated with pressure sensitive adhesives. Note that the inner release liner 46 is shown in place in FIGS. 1 and 2 and removed in FIGS. 3 and 4.

An interface-coupling medium (not shown) may be employed between the electrode assembly and the biological interface 18. The interface-coupling medium may, for example, take the form of an adhesive and/or gel. The gel may, for example, take the form of a hydrating gel. Selection of suitable bioadhesive gels is within the knowledge of one skilled in the art.

Figure 2:
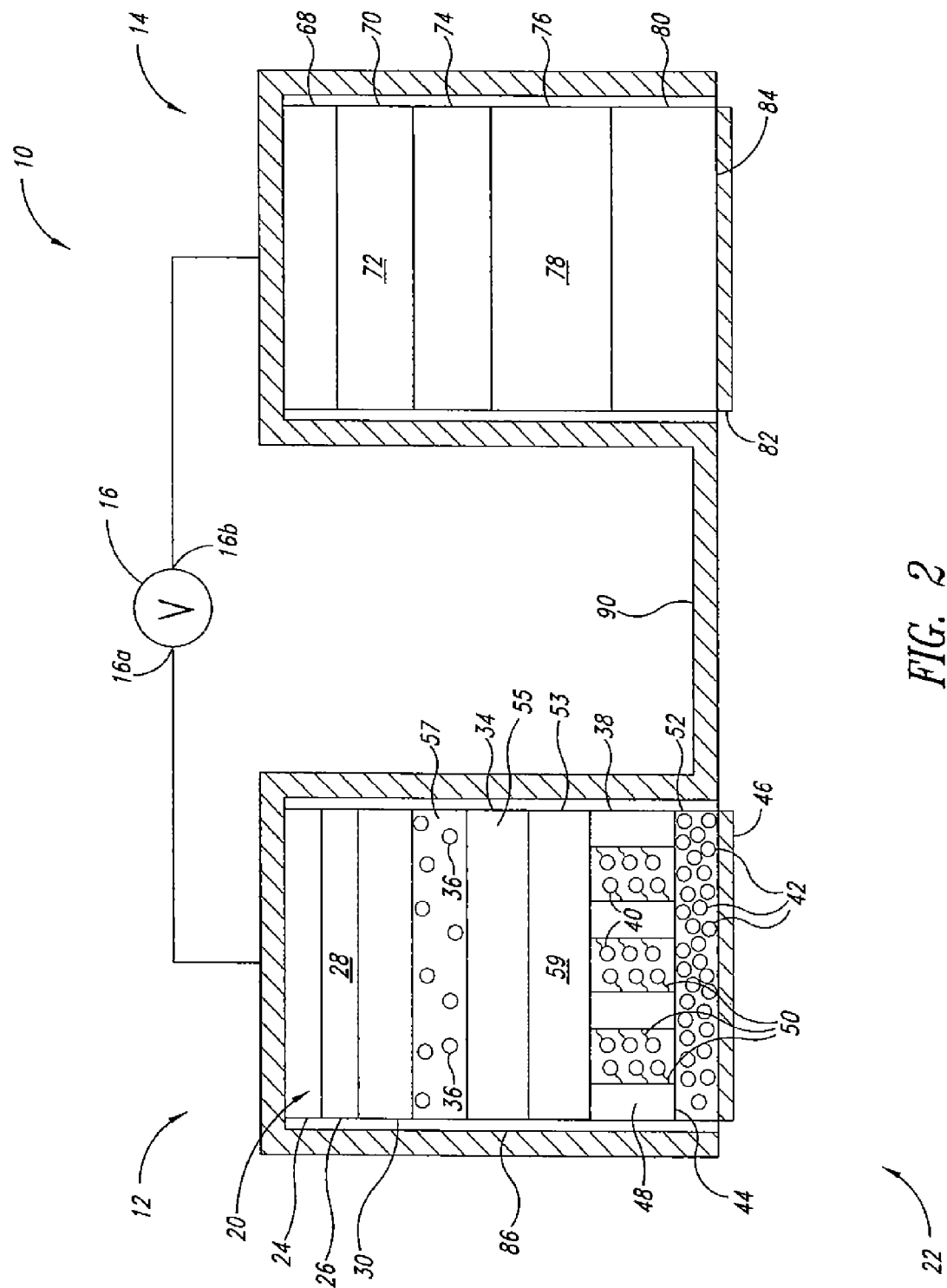
FIG. 2 is a block diagram of an iontophoresis device comprising active and counter electrode assemblies according to one illustrated embodiment, in which the active electrode is an anode.

In the embodiment illustrated in FIG. 2, the active electrode element 24 is an anode. In this embodiment, the diluent compartment 53 and the active agent compartment 57 are switched in their relative positions with respect to the polymer complex layer 55. Under the electrical field, hydroxide ions present in the diluent compartment 53 are going to be pulled toward the anode, which leads to the increase of the pH in the vicinity of the polymer complex layer 55. In this embodiment, the active agents are preferably cationic after mixing with the diluent.

Figure 3:
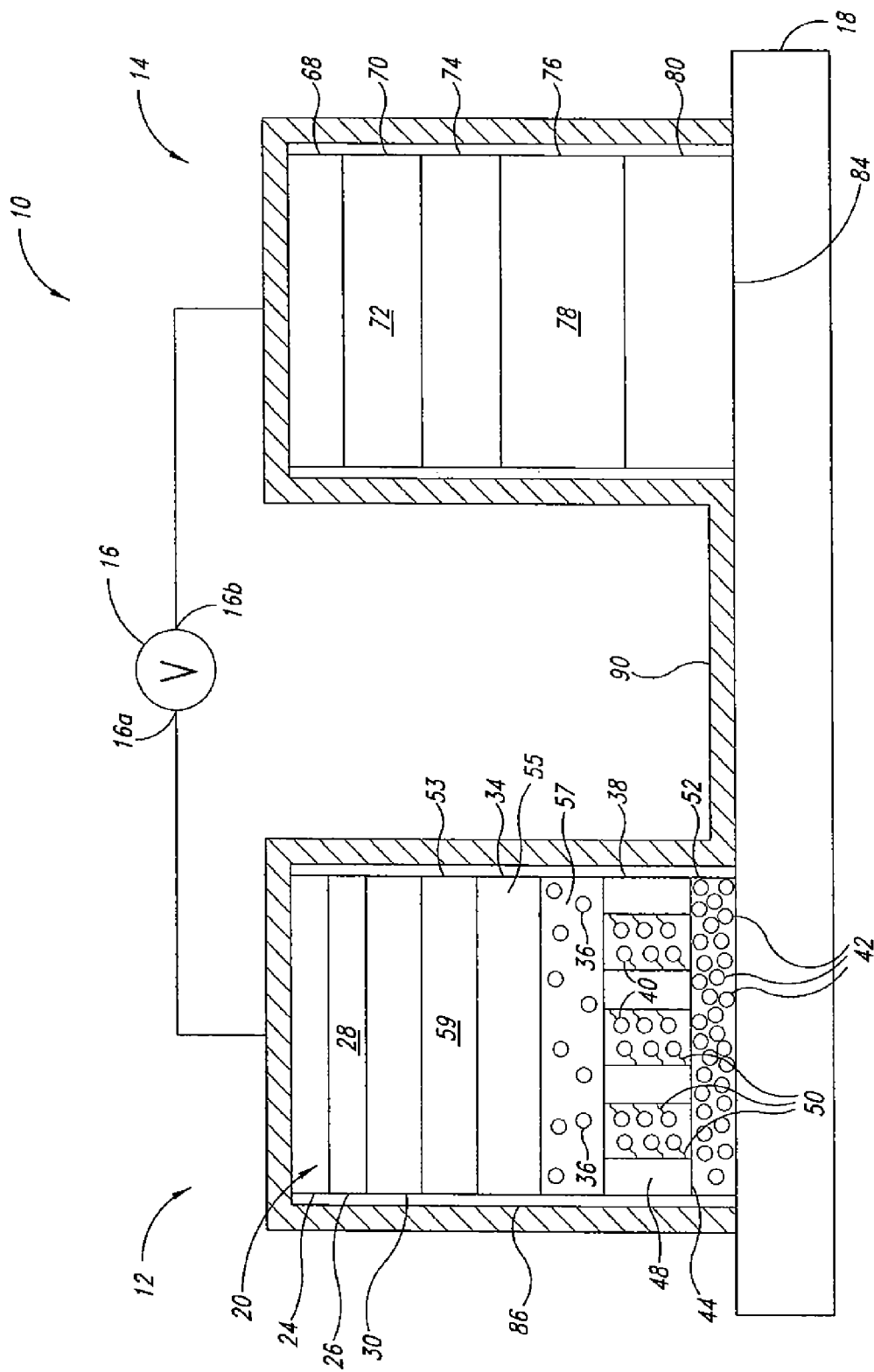
FIG. 3 is a block diagram of the iontophoresis device of FIG. 1 positioned on a biological interface, with the outer release liner removed to expose the active agent according to one illustrated embodiment.
Figure 4:
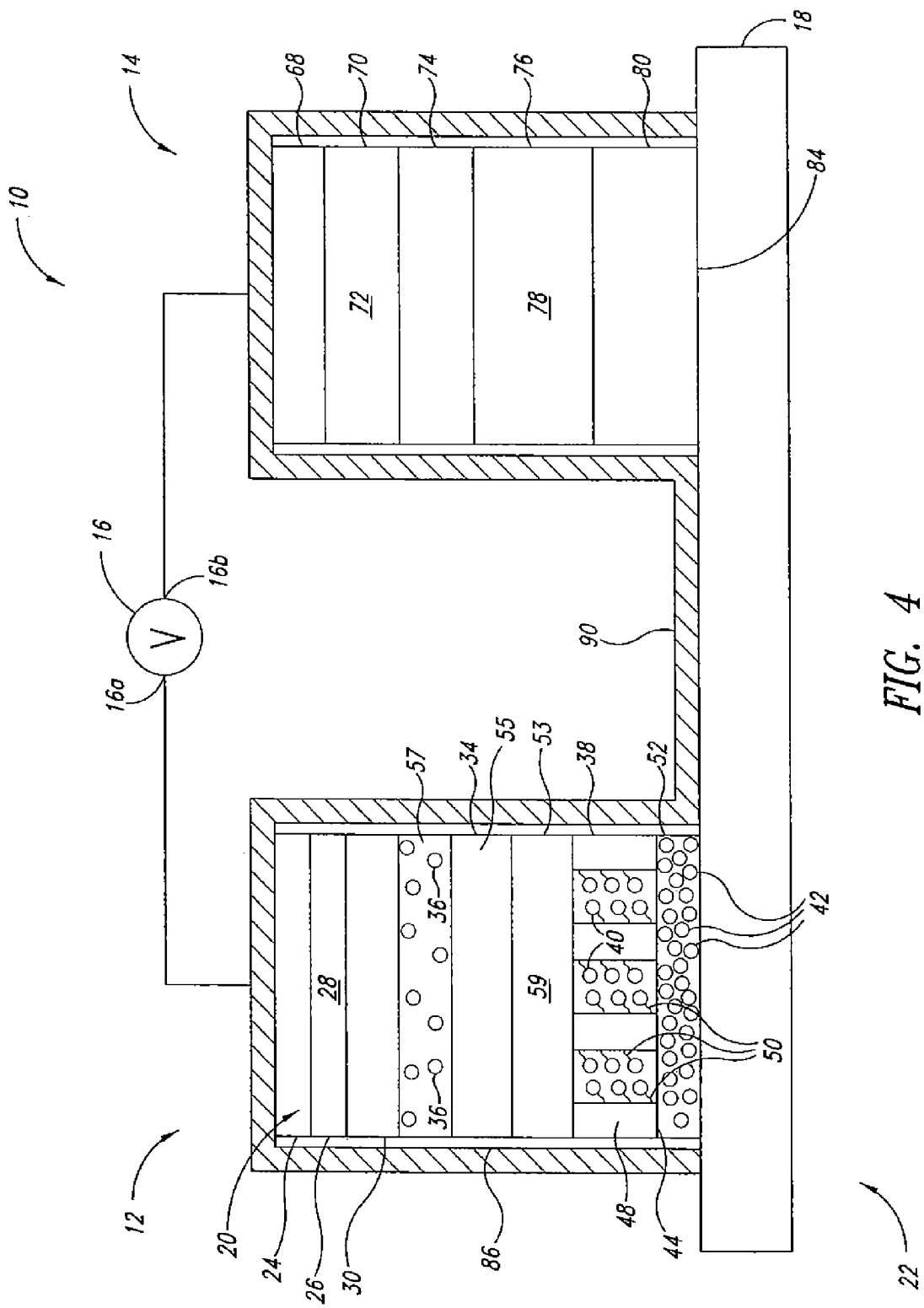
FIG. 4 is a block diagram of the iontophoresis device of FIG. 2 positioned on a biological interface, with the outer release liner removed to expose the active agent according to one illustrated embodiment.

In the embodiments illustrated in FIGS. 3 and 4, a biological surface 18 is shown to be in contact with the outer surface 44 of the outermost ion selective membrane 38.

FIGS. 3 and 4 further illustrate a counter electrode assembly 14, which comprises, in an order from an interior 64 to an exterior 66 of the counter electrode assembly 14: a counter electrode element 68, electrolyte reservoir 70 storing an electrolyte 72, an inner ion selective membrane 74, an optional buffer reservoir 76 storing buffer material 78, an optional outermost ion selective membrane 80, and an optional outer release liner 82.

The counter electrode element 68 is electrically coupled to a second pole 16*b* of the power source 16, the second pole 16*b* having an opposite polarity to the first pole 16*a*. The counter electrode element 68 is therefore the anode of the device of FIG. 1, and cathode of the device of FIG. 2. In one embodiment, the counter electrode element 68 is an inert electrode. For example, the counter electrode element 68 may be the carbon-based electrode element discussed above.

The electrolyte reservoir 70 may take a variety of forms including any structure capable of retaining electrolyte 72, and in some embodiments may even be the electrolyte 72 itself, for example, where the electrolyte 72 is in a gel, semi-solid or solid form. For example, the electrolyte reservoir 70 may take the form of a pouch or other receptacle, or a membrane with pores, cavities or interstices, particularly where the electrolyte 72 is a liquid.

The electrolyte 72 is generally positioned between the counter electrode element 68 and the outermost ion selective membrane 80, proximate the counter electrode element 68. As described above, the electrolyte 72 may provide ions or donate charges to prevent or inhibit the formation of gas bubbles (e.g., hydrogen or oxygen, depending on the polarity of the electrode) on the counter electrode element 68 and may prevent or inhibit the formation of acids or bases or neutralize the same, which may enhance efficiency and/or reduce the potential for irritation of the biological interface 18.

The inner ion selective membrane 74 is positioned between and/or to separate, the electrolyte 72 from the buffer material 78. The inner ion selective membrane 74 may take the form of a charge selective membrane, such as the illustrated ion exchange membrane that substantially allows passage of ions of a first polarity or charge while substantially blocking passage of ions or charge of a second, opposite polarity. The inner ion selective membrane 74 will typically pass ions of opposite polarity or charge to those passed by the outermost ion selective membrane 80 while substantially blocking ions of like polarity or charge. Alternatively, the inner ion selective membrane 74 may take the form of a semi-permeable or microporous membrane that is selective based on size.

The inner ion selective membrane 74 may prevent transfer of undesirable elements or compounds into the buffer material 78. For example, the inner ion selective membrane 74 may prevent or inhibit the transfer of hydroxy ($OH^-$) or chloride ($Cl^-$) ions from the electrolyte 72 into the buffer material 78.

The optional buffer reservoir 76 is generally disposed between the electrolyte reservoir and the outermost ion selective membrane 80. The buffer reservoir 76 may take a variety of forms capable of temporarily retaining the buffer material 78. For example, the buffer reservoir 76 may take the form of a cavity, a porous membrane or a gel.

The buffer material 78 may supply ions for transfer through the outermost ion selective membrane 42 to the biological interface 18. Consequently, the buffer material 78 may, for example, comprise a salt (e.g., NaCl).

The outermost ion selective membrane 80 of the counter electrode assembly 14 may take a variety of forms. For example, the outermost ion selective membrane 80 may take the form of a charge selective ion exchange membrane. Typically, the outermost ion selective membrane 80 of the counter electrode assembly 14 is selective to ions with a charge or polarity opposite to that of the outermost ion selective membrane 38 of the active electrode assembly 12. The outermost ion selective membrane 80 is therefore an anion exchange membrane, which substantially passes anions and blocks cations, thereby prevents the back flux of the cations from the biological interface. Examples of suitable ion exchange membranes are discussed above.

Alternatively, the outermost ion selective membrane 80 may take the form of a semi-permeable membrane that substantially passes and/or blocks ions based on size or molecular weight of the ion.

The outer release liner 82 may generally be positioned overlying or covering an outer surface 84 of the outermost ion selective membrane 80. Note that the inner release liner 82 is shown in place in FIG. 1 and removed in FIG. 2. The outer release liner 82 may protect the outermost ion selective membrane 80 during storage, prior to application of an electromotive force or current. The outer release liner 82 may be a selectively releasable liner made of waterproof material, such as release liners commonly associated with pressure sensitive adhesives. In some embodiments, the outer release liner 82 may be coextensive with the outer release liner 46 of the active electrode assembly 12.

The iontophoresis device 10 may further comprise an inert molding material 86 adjacent exposed sides of the various other structures forming the active and counter electrode assemblies 12, 14. The molding material 86 may advantageously provide environmental protection to the various structures of the active and counter electrode assemblies 12, 14.

As best seen in FIGS. 3-4, the active and counter electrode assemblies 12, 14 are positioned on the biological interface 18. Positioning on the biological interface may close the circuit, allowing electromotive force and/or current to be applied and/or current to flow from one pole 16a of the power source 16 to the other pole 16b, via the active electrode assembly, biological interface 18 and counter electrode assembly 14.

In the presence of the electromotive force and/or current, hydroxide ions generated by electrolysis of the diluent in the diluent compartment will migrate toward the polymer complex layer 55 and increase the local pH. The polymer complex layer 55 disintegrates and allows for the mixing of the diluent 59 and the active agents 36 within the active agent reservoir 34. Optionally, additional active agent 40 is released by the ion exchange groups or material 50 by the substitution of ions of the same charge or polarity (e.g., active agent 36), and transported toward the biological interface 18. While some of the active agent 36 may substitute for the additional active agent 40, some of the active agent 36 may be transferred through the outermost ion elective membrane 38 into the biological interface 18. Further optional active agent 42 carried by the outer surface 44 of the outermost ion elective membrane 38 is also transferred to the biological interface 18.

In use, the outermost active electrode ion selective membrane 38 may be placed directly in contact with the biological interface 18. Alternatively, an interface-coupling medium (not shown) may be employed between the outermost active electrode ion selective membrane 22 and the biological interface 18. The interface-coupling medium may, for example, take the form of an adhesive and/or gel. The gel may, for example, take the form of a hydrating gel or a hydrogel. If used, the interface-coupling medium should be permeable by the active agent 36.

The power source 16 may take the form of one or more chemical battery cells, super- or ultra-capacitors, or fuel cells. The power source 16 may, for example, provide a voltage of 12.8V DC, with tolerance of 0.8V DC, and a current of 0.3 mA. The power source 16 may be selectively electrically coupled to the active and counter electrode assemblies 12, 14 via a control circuit, for example, via carbon fiber ribbons. The iontophoresis device 10a may include discrete and/or integrated circuit elements to control the voltage, current and/or power delivered to the electrode assemblies 12, 14. For example, the iontophoresis device 10 may include a diode to provide a constant current to the electrode elements 20, 40.

Other embodiments describe a method for transdermal administration of an active agent by iontophoresis, comprising:

positioning an active electrode assembly and a counter electrode assembly of an iontophoresis device on a biological interface of a subject, the active electrode assembly further including an active electrode element operable to provide an electrical potential; and an inner active agent reservoir comprising a first compartment having a diluent, a second compartment having an active agent, and a polymer complex layer disposed between the first and second compartments, the polymer complex being formed by a first hydrophilic polymer and a second hydrophilic polymer via hydrogen bonding; and applying a sufficient amount of current to cause the polymer complex layer to disintegrate such that the diluent and the active agent are mixed, and to administer a therapeutically effective amount of the active agent in the subject for a limited period of time.

In certain embodiments, the application of the electrical current causes the formation of hydroxide ions. For instance, when the active electrode element is a cathode, hydroxide ions are generated electrochemically at the active electrode assembly. The hydroxide ions are caused to migrate away from the cathode and toward the polymer complex layer. As a result, the local pH in the vicinity of the polymer complex layer increase, which in turn causes the weakening or elimination of the hydrogen bonding.

The above description of illustrated embodiments, including what is described in the Abstract, is not intended to be exhaustive or to limit the claims to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to other agent delivery systems and devices, not necessarily the exemplary iontophoresis active agent system and devices generally described above. For instance, some embodiments may include additional structure. For example, some embodiment may include a control circuit or subsystem to control a voltage, current or power applied to the active and counter electrode elements 20, 40. Also for example, some embodiments may include an interface layer interposed between the outermost active electrode ion selective membrane 38 and the biological interface 18. Some embodiments may comprise additional ion selective membranes, ion exchange membranes, semi-permeable membranes and/or porous membranes, as well as additional reservoirs for electrolytes and/or buffers. Some embodiments may omit one or more of the reservoirs, membranes and/or other structures.

Various electrically conductive hydrogels have been known and used in the medical field to provide an electrical interface to the skin of a subject or within a device to couple electrical stimulus into the subject. Hydrogels hydrate the skin, thus protecting against burning due to electrical stimulation through the hydrogel, while swelling the skin and allowing more efficient transfer of an active component. Examples of such hydrogels are disclosed in U.S. Pat. Nos. 6,803,420; 6,576,712; 6,908,681; 6,596,401; 6,329,488; 6,197,324; 5,290,585; 6,797,276; 5,800,685; 5,660,178; 5,573,668; 5,536,768; 5,489,624; 5,362,420; 5,338,490; and 5,240,995, herein incorporated in their entirety by reference. Further examples of such hydrogels are disclosed in U.S. patent applications Ser. Nos. 2004/166147; 2004/105834; and 2004/247655, herein incorporated in their entirety by reference. Product brand names of various hydrogels and hydrogel sheets include Corplex™ by Corium, Tegagel™ by 3M, PuraMatrix™ by BD; Vigilon™ by Bard; ClearSite™ by Conmed Corporation; FlexiGel™ by Smith & Nephew; Derma-Gel™ by Medline; Nu-Gel™ by Johnson & Johnson; and Curagel™ by Kendall, or acrylhydrogel films available from Sun Contact Lens Co., Ltd.

The iontophoresis device discussed above may advantageously be combined with other microstructures, for example microneedles. Microneedles and microneedle arrays, their manufacture, and use have been described. Microneedles, either individually or in arrays, may be hollow; solid and permeable; solid and semi-permeable; or solid and non-permeable. Solid, non-permeable microneedles may further comprise grooves along their outer surfaces. Microneedle arrays, comprising a plurality of microneedles, may be arranged in a variety of configurations, for example rectangular or circular. Microneedles and microneedle arrays may be manufactured from a variety of materials, including silicon; silicon dioxide; molded plastic materials, including biodegradable or non-biodegradable polymers; ceramics; and metals. Microneedles, either individually or in arrays, may be used to dispense or sample fluids through the hollow apertures, through the solid permeable or semi-permeable materials, or via the external grooves. Microneedle devices are used, for example, to deliver a variety of compounds and compositions to the living body via a biological interface, such as skin or mucous membrane. In certain embodiments, the compounds and drugs may be delivered into or through the biological interface. For example, in delivering compounds or compositions via the skin, the length of the microneedle(s), either individually or in arrays, and/or the depth of insertion may be used to control whether administration of a compound or composition is only into the epidermis, through the epidermis to the dermis, or subcutaneous. In certain embodiments, microneedle devices may be useful for delivery of high-molecular weight compounds and drugs, such as those comprising proteins, peptides and/or nucleic acids, and corresponding compositions thereof. In certain embodiments, for example wherein the fluid is an ionic solution, microneedle(s) or microneedle array(s) can provide electrical continuity between a voltage source and the tip of the microneedle(s). Microneedle(s) or microneedle array(s) may be used advantageously to deliver or sample compounds or compositions by iontophoretic methods, as disclosed herein.

Accordingly, in certain embodiments, for example, a plurality of microneedles in an array may advantageously be formed on an outermost biological interface-contacting the outer surface of an iontophoresis device. Active agents delivered or sample by such a device may comprise, for example, high-molecular weight molecules or drugs, such as proteins, peptides and/or nucleic acids.

In certain embodiments, compounds or compositions can be delivered by an iontophoresis device comprising an active electrode assembly and a counter electrode assembly, electrically coupled to a voltage source to deliver an active agent to, into, or through a biological interface. The active electrode assembly includes the following: a first electrode member connected to a positive electrode of the voltage source; an active agent reservoir having a drug solution that is in contact with the first electrode member and to which is applied a voltage via the first electrode member; a biological interface contact member, which may be a microneedle array and is placed against the forward surface of the active agent reservoir; and a first cover or container that accommodates these members. The counter electrode assembly includes the following: a second electrode member connected to a negative electrode of the voltage source; a second electrolyte holding part that holds an electrolyte that is in contact with the second electrode member and to which voltage is applied via the second electrode member; and a second cover or container that accommodates these members.

In certain other embodiments, compounds or compositions can be delivered by an iontophoresis device comprising an active electrode assembly and a counter electrode assembly, electrically coupled to a voltage source to deliver an active agent to, into, or through a biological interface. The active electrode assembly includes the following: a first electrode member connected to a positive electrode of the voltage source; a first electrolyte holding part having an electrolyte that is in contact with the first electrode member and to which is applied a voltage via the first electrode member; a first anion-exchange membrane that is placed on the forward surface of the first electrolyte holding part; an active agent reservoir that is placed against the forward surface of the first anion-exchange membrane; a biological interface contacting member, which may be a microneedle array and is placed against the forward surface of the active agent reservoir; and a first cover or container that accommodates these members. The counter electrode assembly includes the following: a second electrode member connected to a negative electrode of the voltage source; a second electrolyte holding part having an electrolyte that is in contact with the second electrode member and to which is applied a voltage via the second electrode member; a cation-exchange membrane that is placed on the forward surface of the second electrolyte holding part; a third electrolyte holding part that is placed against the forward surface of the cation-exchange membrane and holds an electrolyte to which a voltage is applied from the second electrode member via the second electrolyte holding part and the cation-exchange membrane; a second anion-exchange membrane placed against the forward surface of the third electrolyte holding part; and a second cover or container that accommodates these members.

Certain details of microneedle devices, their use and manufacture, are disclosed in U.S. Pat. Nos. 6,256,533; 6,312,612; 6,334,856; 6,379,324; 6,451,240; 6,471,903; 6,503,231; 6,511,463; 6,533,949; 6,565,532; 6,603,987; 6,611,707; 6,663,820; 6,767,341; 6,790,372; 6,815,360; 6,881,203; 6,908,453; 6,939,311; all of which are incorporated herein by reference in their entirety. Some or all of the teaching therein may be applied to microneedle devices, their manufacture, and their use in iontophoretic applications.

Aspects of the various embodiments can be modified, if necessary, to employ systems, circuits and concepts of the various patents, applications and publications to provide yet further embodiments, including those patents and applications identified herein. While some embodiments may include all of the membranes, reservoirs and other structures discussed above, other embodiments may omit some of the membranes, reservoirs or other structures. Still other embodiments may employ additional ones of the membranes, reservoirs and structures generally described above. Even further embodiments may omit some of the membranes, reservoirs and structures described above while employing additional ones of the membranes, reservoirs and structures generally described above.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety, including but not limited to: Japanese patent application Serial No. H03-86002, filed Mar. 27, 1991, having Japanese Publication No. H04-297277, issued on Mar. 3, 2000 as Japanese Patent No. 3040517; Japanese patent application Serial No. 11-033076, filed Feb. 10, 1999, having Japanese Publication No. 2000-229128; Japanese patent application Serial No. 11-033765, filed Feb. 12,1999, having Japanese Publication No. 2000-229129; Japanese patent application Serial No. 11-041415, filed Feb. 19, 1999, having Japanese Publication No. 2000-237326; Japanese patent application Serial No. 11-041416, filed Feb. 19, 1999, having Japanese Publication No. 2000-237327; Japanese patent application Serial No. 11-042752, filed Feb. 22, 1999, having Japanese Publication No. 2000-237328; Japanese patent application Serial No. 11-042753, filed Feb. 22, 1999, having Japanese Publication No. 2000-237329; Japanese patent application Serial No. 11-099008, filed Apr. 6, 1999, having Japanese Publication No. 2000-288098; Japanese patent application Serial No. 11-099009, filed Apr. 6, 1999, having Japanese Publication No. 2000-288097; PCT patent application WO 2002JP4696, filed May 15, 2002, having PCT Publication No WO03037425; U.S. patent application Serial No. 10/488970, filed Mar. 9, 2004; U.S. Provisional Patent Application No. 60/722,790, filed on Sep. 30, 2005; Japanese patent application 2004/317317, filed Oct. 29, 2004; U.S. provisional patent application Serial No. 60/627,952, filed Nov. 16, 2004; Japanese patent application Serial No. 2004-347814, filed Nov. 30, 2004; Japanese patent application Serial No. 2004-357313, filed Dec. 9, 2004; Japanese patent application Serial No. 2005-027748, filed Feb. 3, 2005; and Japanese patent application Serial No. 2005-081220, filed Mar. 22, 2005.

Aspects of the various embodiments can be modified, if necessary, to employ systems, circuits and concepts of the various patents, applications and publications to provide yet further embodiments.

These and other changes can be made in light of the above-detailed description. In general, in the following claims, the terms used should not be construed to be limiting to the specific embodiments disclosed in the specification and the claims, but should be construed to include all systems, devices and/or methods that operate in accordance with the claims. Accordingly, the invention is not limited by the disclosure, but instead its scope is to be determined entirely by the following claims.

I claim:

1. An iontophoresis device for delivering active agents to a biological interface, the iontophoresis device comprising an active electrode assembly and a counter electrode assembly, the active electrode assembly further including:
    an active electrode element operable to provide an electrical potential; and
    an inner active agent reservoir comprising:
        a first compartment having a diluent;
        a second compartment having an active agent; and
        a polymer complex layer disposed between the first compartment and the second compartment, the polymer complex being formed by a first hydrophilic polymer and a second hydrophilic polymer via hydrogen bonding, wherein, when the electrical potential is applied to the active electrode, the polymer complex layer disintegrates to allow the active agent and the diluent to mix.

2. The iontophoresis device of claim 1 wherein the first hydrophilic polymer comprising a plurality of electron-deficient groups.

3. The iontophoresis device of claim 1 wherein the second hydrophilic polymer comprising a plurality of electron-rich groups.

4. The iontophoresis device of claim 1 where the polymer complex is a complex of poly((meth)acrylic acid) and poly(acrylamide), a complex of poly((meth)acrylic acid) and poly(vinyl alcohol), a complex of poly((meth)acrylic acid) and poly(ethylene glycol), a complex of poly((meth)acrylic acid) and poly(N-vinylpyrrolidone) or a complex of poly((meth)acrylic acid) and poly(ethyloxazoline).

5. The iontophoresis device of claim 4 wherein the polymer complex forms at a critical pH value.

6. The iontophoresis device of claim 5 wherein, when the electrical potential is applied to the active electrode, hydroxide ions migrate toward the polymer complex layer to increase a local pH value, and the polymer complex layer disintegrates when the local pH reaches above the critical pH value.

7. The iontophoresis device of claim 1 wherein the polymer complex is in solid form.

8. The iontophoresis device of claim 1 wherein the polymer complex is in gel form.

9. The iontophoresis device of claim 1 wherein the diluent is aqueous.

10. The iontophoresis device of claim 1 wherein the active agent is in solid form.

11. The iontophoresis device of claim 1 wherein the active agent is in a stable solution form.

12. The iontophoresis device of claim 1 wherein the active agent is more stable in the second compartment than when it is mixed with the diluent.

13. The iontophoresis device of claim 1, further comprising: an electrolyte reservoir disposed between the active electrode element and the inner active agent reservoir.

14. The iontophoresis device of claim 1, further comprising: an inner ion selective membrane disposed between said electrolyte reservoir and said inner active agent reservoir.

15. The iontophoresis device of claim 1, further comprising: an outermost ion selective membrane having an outer surface, the outer surface being proximate the biological interface when in use.

16. The iontophoresis device of claim 15, further comprising: a second active agent cached in the outermost ion selective membrane.

17. The iontophoresis device of claim 15, further comprising: a third active agent deposited on the out surface of the outermost ion selective membrane.

18. The iontophoresis device of claim 15, further comprising: an outer release liner underlying said outer surface, said outer release liner being proximate the biological interface when in use.

19. The iontophoresis device of claim 1, further comprising: a microneedle array contacting an outer surface of the iontophoresis device.

20. A method for transdermal administration of an active agent by iontophoresis, comprising:
    positioning an active electrode assembly and a counter electrode assembly of an iontophoresis device on a biological interface of a subject, the active electrode assembly further including an active electrode element operable to provide an electrical potential; and an inner active agent reservoir comprising a first compartment having a diluent, a second compartment having an active agent, and a polymer complex layer disposed between the first compartment and the second compartment, the polymer complex being formed by a first hydrophilic polymer and a second hydrophilic polymer via hydrogen bonding; and
    applying a sufficient amount of electrical current to cause the polymer complex layer to disintegrate such that the diluent and the active agent are mixed, and to administer a therapeutically effective amount of the active agent in the subject for a limited period of time.

21. The method of claim 20 wherein applying the sufficient amount of current includes electrochemically reducing water to produce hydroxide ions.

22. The method of claim 21 wherein the hydroxide ions weaken the hydrogen bonding and cause the polymer complex layer to disintegrate.

23. The method of claim 21 wherein the active agent is more stable in the second compartment than when it is mixed with the diluent.

24. The method of claim 21 where the polymer complex is a complex of poly((meth)acrylic acid) and poly(acrylamide), a complex of poly((meth)acrylic acid) and poly(vinyl alcohol), a complex of poly((meth)acrylic acid) and poly(ethylene glycol), a complex of poly((meth)acrylic acid) and poly(N-vinylpyrrolidone) or a complex of poly((meth)acrylic acid) and poly(ethyloxazoline).

* * * * *